United States Patent [19]

Turk et al.

[11] 4,232,027
[45] Nov. 4, 1980

[54] 1,2-DIHYDRO-2-OXO-4-PHENYL-3-QUINOLINECARBONITRILE DERIVATIVES

[75] Inventors: Chester F. Turk, Kendall Park; John Krapcho, Somerset, both of N.J.

[73] Assignee: E. R. Squibb & Sons, Inc., Princeton, N.J.

[21] Appl. No.: 7,069

[22] Filed: Jan. 29, 1979

[51] Int. Cl.³ .................. C07D 215/20; C07D 413/06; A61K 31/47
[52] U.S. Cl. .................... 424/258; 544/128; 546/157
[58] Field of Search ............ 546/157; 544/128; 424/248.56, 258

[56] References Cited

U.S. PATENT DOCUMENTS

| | | | |
|---|---|---|---|
| 3,210,358 | 10/1965 | Pfister et al. | 546/157 |
| 3,763,153 | 10/1973 | Krapcho et al. | 424/248.56 X |
| 3,895,006 | 7/1975 | Krapcho et al. | 424/275 X |
| 3,994,900 | 11/1976 | Krapcho et al. | 544/128 X |

FOREIGN PATENT DOCUMENTS 1121411  7/1968  United Kingdom ............ 546/155

OTHER PUBLICATIONS

Ziegler, et al., C. A., 68, 1968, p. 12832q.
Ziegler, et al., Monatsh. Chem., 96(4), 1965, pp. 1252–1260.

*Primary Examiner*—Joseph Paul Brust
*Attorney, Agent, or Firm*—Lawrence S. Levinson; Burton Rodney

[57] ABSTRACT

1,2-Dihydro-2-oxo-4-phenyl-3-quinolinecarbonitrile derivatives are provided having the structure

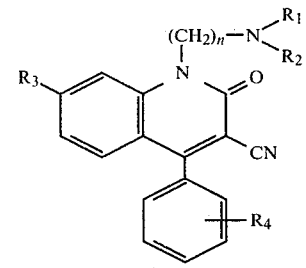

wherein $(CH_2)_n$ represents a straight chain alkylene group containing 2 to 5 carbons, and $R_1$ and $R_2$ are the same or different and may be hydrogen or lower alkyl with the proviso that at least one of $R_1$ and $R_2$ is lower alkyl, or

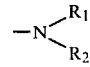

can be taken together to form a heterocyclic radical containing 5- or 6-members in the heterocyclic ring, such as pyrrolidino, piperidino or morpholino, and $R_3$ and $R_4$ may be the same or different and are hydrogen, lower alkyl, lower alkoxy, halogen or trifluoromethyl, and physiologically acceptable acid addition salts thereof. These compounds are useful as anti-inflammatory agents. A pharmaceutical composition containing the above compounds and a method of use are also provided.

9 Claims, No Drawings

1,2-DIHYDRO-2-OXO-4-PHENYL-3-QUINOLINECARBONITRILE DERIVATIVES

DESCRIPTION OF THE INVENTION

The present invention relates to compounds of the structure

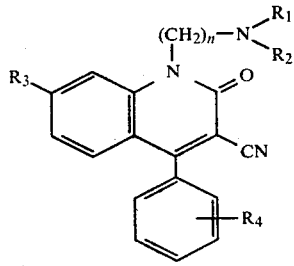

wherein $(CH_2)_n$ is a straight chain containing 2 to 5 carbons, and $R_1$ and $R_2$ are the same or different and are hydrogen or lower alkyl, with the proviso that at least one of $R_1$ and $R_2$ is lower alkyl, or

can be taken together to form a heterocyclic radical containing 5- or 6-members in the heterocyclic ring, and $R_3$ and $R_4$ may be the same or different and may be hydrogen, lower alkyl, lower alkoxy, halogen or trifluoromethyl, and physiologically acceptable acid-addition salts thereof. These compounds are useful as antiinflammatory agents.

In the above compounds, $(CH_2)_n$ represents a straight chain alkylene hydrocarbon group having from 2 to 5 carbons, such as $(CH_2)_2$, $(CH_2)_3$, $(CH_2)_4$ or $(CH_2)_5$.

As indicated hereinbefore,

may form a 5- or 6-membered nitrogen-containing heterocyclic radical. Examples of such heterocyclic radicals include pyrrolidino, piperidino or morpholino.

Unless otherwise indicated, the term "lower alkyl" or "alkyl" as employed herein includes both straight and branched chain radicals of up to eight carbon atoms, preferably up to and including 5 carbon atoms, for instance, methyl, ethyl, n-propyl, isopropyl, n-butyl, t-butyl, isobutyl, n-pentyl, n-hexyl, isohexyl, n-heptyl, 4,4-dimethylpentyl, n-octyl, 2,2,4-trimethylpentyl, and the like.

The term "lower alkoxy" refers to any of the above "lower alkyl" groups attached to an oxygen atom.

The term "halogen" refers to Cl, Br or F, with Cl being preferred.

Preferred are those compounds of formula I wherein $(CH_2)_n$ is $(CH_2)_2$ or $(CH_2)_3$, $R_1$ and $R_2$ are each methyl or ethyl, and at least one of $R_3$ and $R_4$ is hydrogen or both $R_3$ and $R_4$ are hydrogen.

The compounds of the invention may be prepared as follows.

Compounds of formula I wherein

is dialkylamine or forms a N-containing heterocyclic radical as defined above may be prepared by reacting 1,2-dihydro-2-oxo-4-phenyl-3-quinolinecarbonitrile, that is

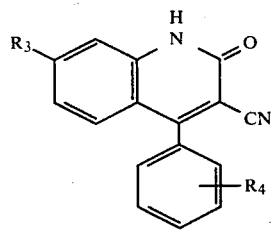

with an alkali metal hydride, such as sodium or potassium hydride, and an aminoalkylene halide of the structure

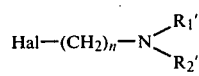

wherein Hal represents Cl or Br, $(CH_2)_n$ is an alkylene group as defined hereinbefore, and

represents dialkylamino, or a N-containing heterocyclic group such as pyrrolidino, piperidino or morpholino, to form a compound of the invention of the structure

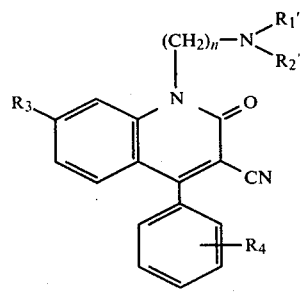

The above reaction is carried out employing a molar ratio of the aminoalkylene halide III to 1,2-dihydro-2-oxo-4-phenyl-3-quinolinecarbonitrile II of within the range of from about 1.1:1 to about 1.3:1, at a temperature within the range of from about 80° to about 100° C., in the presence of a solvent such as dimethylformamide, dimethylsulfoxide, toluene or benzene.

Compounds of the invention of formula I wherein one of $R_1$ and $R_2$ is lower alkyl and the other is hydrogen, that is,

represents a monoalkylamino group, may be prepared as described above except that the aminoalkylene halide employed preferably comprises a benzylamino alkylene halide of the structure

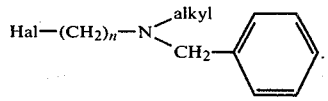

Compound V is reacted with the 1,2-dihydro-2-oxo-4-phenyl-3-quinolinecarbonitrile to form a benzylamino intermediate of the structure

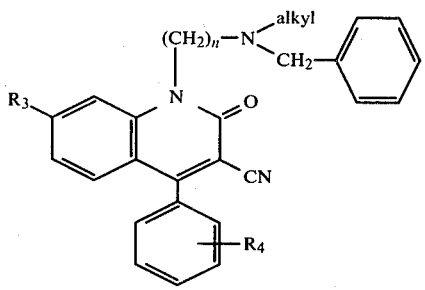

The intermediate VI is subjected to catalytic hydrogenation in the presence of a palladium/carbon catalyst or platinum catalyst to remove the benzyl group and form compounds of the invention of the structure

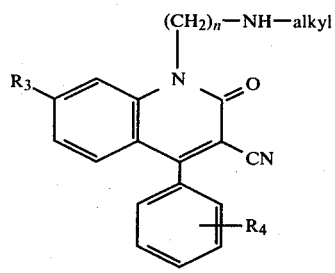

The quinolinecarbonitrile starting material II may be prepared by heating 2-aminobenzophenone with ethyl cyanoacetate, in accordance with the procedure of Ziegler and Wimmer, Monatsh. Chem. 96(4), 1252–60 (1965) (Ger), C.A. 68:12832q, (1968).

Alternatively, the starting material II may be prepared by reacting 2,3-dihydro-2-phenyl-1,5-benzothiazepin-4(5H)-one (prepared as disclosed by Krapcho et al, J. Med. Chem., 6, 544 (1963)) with N-bromosuccinimide to form 3-bromo-2-phenyl-1,5-benzothiazepin-4(5H)-one which is then reacted with cuprous cyanide in the presence of a solvent such as dimethylformamide to form the 1,2-dihydro-2-oxo-4-phenyl-3-quinolinecarbonitrile starting material.

In another synthesis of the formula I compounds of the invention, 5-(substituted aminoalkyl)-2-aryl-3-halo-1,5-benzothiazepin-4(5H)-ones as disclosed in U.S. Pat. No. 3,895,006, namely,

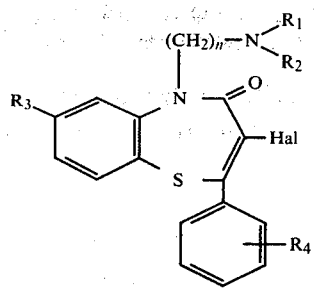

wherein $R_1$, $R_2$, $R_3$ and $R_4$ are as defined hereinbefore, is reacted with cuprous cyanide in dimethylformamide.

The compounds of formula I form acid-addition salts by reaction with various inorganic and organic acids. These salts frequently provide convenient means for separating the product from the reaction mixture in which it is produced or from the solvent in which it is extracted in view of their insolubility in various media. Thus, the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acids salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The formula I compounds have antiinflammatory activity as measured by the mouse active arthus (MAA) test and/or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. For this purpose these compounds may be incorporated in a conventional dosage form such as tablet, capsule, injectable or the like, along with the necessary carrier material, excipient, lubricant, buffer or the like, as will be seen hereinafter, for oral or parenteral administration in single or divided doses of about 1 to 150 mg/kg/day, preferably about 5 to 75 mg/kg, two to four times daily.

The compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples represent preferred embodiments of the present invention. All temperatures are expressed in degrees Centigrade (°C.).

EXAMPLE 1

1-[3-(Dimethylamino)propyl]-1,2-dihydro-2-oxo-4-phenyl-3-quinolinecarbonitrile

A. 1,2-Dihydro-2-oxo-4-phenyl-3-quinolinecarbonitrile

Ref. Procedure: Monatsh. Chem., 96, 1259 (1965).

A mixture of 8.0 g (0.041 mole) of o-aminobenzophenone and 9.6 g (0.085 mole) of ethyl cyanoacetate is heated in an oil bath. After heating at 229°–234° for 1 hour, the molten mass is allowed to cool during which time rapid crystallization occurs. The mixture is stirred with 70 ml of boiling MeCN, and allowed to cool in the cold room overnight. A pale yellow solid is obtained which is filtered, washed with cold MeCN, and air-dried; wt., 7.9 g (79%); m.p. 265°–267°. Lit m.p. 271°.

B. 1-[3-(Dimethylamino)propyl]-1,2-dihydro-2-oxo-4-phenyl-3-quinolinecarbonitrile A stirred suspension of the above quinolone (7.9 g; 0.032 mole) in 45 ml of dimethylformamide is treated with 1.7 g (0.035 mole) of 50% NaH, (temperature kept below 40°), warmed to 70°, cooled to 25°, treated with 27 ml (0.054 mole) of a 1.98 N toluene solution of 3-dimethylaminopropyl chloride, followed by 400 mg of NaI, and heated at 100°–105° for 3 hours.

After standing overnight at room temperature, the mixture is poured into a stirred mixture of 400 ml of cold $H_2O$ and 100 ml of ether to precipitate the solid base. After stirring for 0.5 hour, the solid is filtered, washed with $H_2O$ and with some ether, and air-dried; wt., 5.3 g (45%) of a pale yellow solid, m.p. 185°–187°.

EXAMPLE 2

1-[3-(Dimethylamino)propyl]-1,2-dihydro-2-oxo-4-phenyl-3-quinolinecarbonitrile, hydrochloride A. 3-Bromo-2-phenyl-1,5-benzothiazepin-4(5H)-one A stirred solution of 25.5 g (0.1 mole) of 2,3-dihydro-2-phenyl-1,5-benzothiazepin-4(5H)-one (prepared as disclosed by Krapcho et al, J. Med. Chem., 6, 544, (1963)) in 250 ml of dimethylformamide is treated with a solution of 35 g (0.2 mole) of N-bromosuccinimide in 100 ml of dimethylformamide. The mixture is stirred at 105°–110° for 5 hours, cooled, and poured into 1.8 liters of cold $H_2O$ to precipitate a solid. After cooling overnight, the latter is filtered, washed with $H_2O$, and air-dried; wt. 29.6 g (89%); m.p. 190°–192°; s. 180°. Following crystallization from a mixture of 30 ml of hot dimethylformamide and 60 ml of MeCN, the colorless solid weighs 17.8 g (53%); m.p. 240°–242° (dec.).

B. 1,2-Dihydro-2-oxo-4-phenyl-3-quinolinecarbonitrile

A stirred mixture of 10 g (0.030 mole) of 3-bromo-2-phenyl-1,5-benzothiazepin-4(5H)-one from part A, 10 g (0.11 mole) of CuCN, and 75 ml of dimethylformamide is treated with 1 ml of pyridine, heated, and the resulting dark solution refluxed for 2 hours. After cooling, the reaction mixture is poured into a vigorously stirred mixture of 600 ml of ice-water, 600 ml of concentrated $NH_4OH$, and 300 ml of $CHCl_3$. Stirring is continued until essentially 2 clear layers are obtained. The layers are separated and the blue aqueous $NH_4OH$ layer is extracted with additional $CHCl_3$ (4×150 ml). The combined organic layers are washed with 10% $NH_4OH$ (2×150 ml), then with 150 ml of $H_2O$, dried ($MgSO_4$), and the solvent evaporated (finally at 1 mm. pressure to remove dimethylformamide) to give 5.9 g of a reddish, partly solid residue. The latter is crystallized from 60 ml of MeCN to give 2.2 g (30%) of a pale yellow solid, m.p. 263°–265°(dec.).

C. 1-[3-(Dimethylamino)propyl]-1,2-dihydro-2-oxo-4-phenyl-3-quinolinecarbonitrile, hydrochloride The above quinolinecarbonitrile (2.1 g; 0.0085 mole) is reacted with 0.44 g (0.0092 mole) of 50% NaH and 7.0 ml (0.014 mole) of a 1.98 N toluene solution of 3-dimethylaminopropyl chloride, and 100 mg of NaI in 12 ml of dimethylformamide according to the procedure outlined in Example 1, part B, to give 1.15 g of solid, m.p. 185°–187° (from EtOH).

A solution of the above base in $CH_2Cl_2$ is treated with 0.7 ml of 5.6 N alcoholic HCl and the solvents are removed on a rotary evaporator. The light yellow foamy residue (1.5 g) is crystallized from 12 ml of warm MeCN to give 1.1 g (36%) of pale yellow-orange material; m.p. 229°–231° (dec), s. 151°.

EXAMPLE 3

1-[2-(Dimethylamino)ethyl]-1,2-dihydro-2-oxo-4-phenyl-3-quinolinecarbonitrile, hydrochloride A stirred mixture of 2.0 g (0.0044 mole) of 3-bromo-5-[2-(dimethylamino)ethyl]-2-phenyl-1,5-benzothiazepin-4(5H)-one, prepared as described in Example 3 of U.S. Pat. No. 3,895,066, 2.0 g (0.022 mole) of CuCN, and 15 ml of dimethylformamide is refluxed for 2 hours, cooled, and the dark solution poured into a mixture of 150 ml of concentrated $NH_4OH$ and 100 g of ice. After stirring with 100 ml of $CHCl_3$, the layers are separated and the blue aqueous phase is extracted with additional $CHCl_3$ (3×50 ml). The combined organic layers are washed with 10% $NH_4OH$ (2×100 ml) and with $H_2O$ (100 ml), dried ($MgSO_4$), and evaporated (finally at 1 mm pressure to remove dimethylformamide) to give 1.3 g of a yellow tacky residue.

The base is dissolved in $CHCl_3$, treated with 1 ml of 5.6 N alcoholic HCl, the solvents evaporated, the semisolid residue rubbed under ether, and the evaporation repeated to give 1.5 g of a light yellow amorphous solid. Crystallization from 50 ml of MeCN (the crude product is dissolved in 100 ml of boiling MeCN and concentrated to 50 ml at which point crystallization begins) yields 0.5 g (32%) of pale yellow solid; m.p. 271°–273° (dec).

EXAMPLE 4

1-[3-(Methylamino)propyl]-1,2-dihydro-2-oxo-4-phenyl-3-quinolinecarbonitrile

A.
1-[3-(Benzyl)(methyl)aminopropyl]-1,2-dihydro-2-oxo-4-phenyl-3-quinolinecarbonitrile Following the procedure of Example 1 except substituting 3-(benzyl)(methyl)aminopropyl chloride for 3-dimethylaminopropyl chloride, the title A compound is obtained.

B.
1-[3-(Methylamino)propyl]-1,2-dihydro-2-oxo-4-phenyl-3-quinolinecarbonitrile A suspension of 10 parts of material from part A in 100 ml of ethanol is treated with 1 part of 5% palladium on carbon and placed under 3 atmospheres of gaseous hydrogen and shaken until one equivalent of hydrogen is consumed. The mixture is filtered to remove the catalyst and the solvent evaporated under reduced pressure to yield the title compound.

EXAMPLES 5 TO 12

Following the procedure of Example 1 except substituting the compound shown in Column I of Table A below for 3-dimethylaminopropyl chloride, the product shown in Column II is obtained.

TABLE A

| | | Column I | | Column II | |
|---|---|---|---|---|---|
| Ex. No. | Hal | $(CH_2)_n$ | $N\genfrac{}{}{0pt}{}{R_1}{R_2}$ | $(CH_2)_n$ | $N\genfrac{}{}{0pt}{}{R_1}{R_2}$ |
| 5. | Cl | $(CH_2)_2$ | $N(C_2H_5)_2$ | as in Column I | |
| 6. | Br | $(CH_2)_3$ | $N(CH_3)(C_2H_5)$ | | |
| 7. | Cl | $(CH_2)_4$ | $N(C_3H_7)_2$ | | |
| 8. | Cl | $(CH_2)_5$ | $N(C_4H_9)_2$ | | |
| 9. | Cl | $(CH_2)_5$ | —N(piperidinyl) | | |
| 10. | Cl | $(CH_2)_3$ | —N(morpholinyl) | | |
| 11. | Cl | $(CH_2)_2$ | —N(pyrrolidinyl) | | |
| 12. | Br | $(CH_2)_2$ | —N(piperidinyl) | | |

EXAMPLES 13 TO 20

Following the procedure of Example 3, except substituting the compound shown in Column I of Table B below for 3-bromo-5-[2-(dimethylamino)ethyl]-2-phenyl-1,5-benzothiazepin-4(5H)-one, the product shown in Column II is obtained.

TABLE B

| | Column I | | Column II | | |
|---|---|---|---|---|---|
| Ex. No. | $R_3$ | $R_4$(position) | $(CH_2)_n$–N(R_1)(R_2) | $R_3$ | $R_4$ $(CH_2)_n$–N(R_1)(R_2) |
| 13. | H | $CH_3$(4) | $(CH_2)_2$–N(CH_3)(CH_3)$ | | as in Column I |
| 14. | $CH_3$ | H | $(CH_2)_3$–$NHC_2H_5$ | | |
| 15. | $CH_3O$ | H | $(CH_2)_2$–N(pyrrolidine) | | |
| 16. | $CF_3$ | H | $(CH_2)_4$–N(morpholine) | | |
| 17. | Cl | Cl | $(CH_2)_2$–N(piperidine) | | |
| 18. | H | $C_2H_5O$(4) | $(CH_2)_2$–N(pyrrolidine) | | |
| 19. | H | $CF_3$(3) | $(CH)_5$–N(morpholine) | | |
| 20. | H | Br(2) | $(CH_2)_2N(C_2H_5)_2$ | | |

EXAMPLES 21 TO 25

Following the procedure of Example 4, except substituting the compound shown in Column I of Table C below for 3-(benzyl)(methyl)aminopropyl chloride, the product shown in Column II is obtained.

TABLE C

| | Column I | | | Column II | | |
|---|---|---|---|---|---|---|
| | Hal–$(CH_2)_n$–N(alkyl)(benzyl) | | | $(CH_2)_n$–NHalkyl (on quinoline-2-one with CN and phenyl) | | |
| Ex. No. | Hal | $(CH_2)_n$ | alkyl | $(CH_2)_n$ | alkyl | |
| 21. | Cl | $(CH_2)_2$ | $C_2H_5$ | as in Column I | | |
| 22. | Cl | $(CH_2)_3$ | $C_3H_7$ | | | |
| 23. | Br | $(CH_2)_4$ | $CH_3$ | | | |
| 24. | Cl | $(CH_2)_5$ | $CH_3$ | | | |
| 25. | Cl | $(CH_2)_3$ | $C_4H_9$ | as in Column I | | |

What is claimed is:
1. A compound of the structure

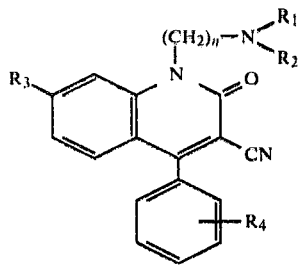

wherein $(CH_2)_n$ is a straight chain alkylene group containing 2 to 5 carbons in the normal chain, and $R_1$ and $R_2$ may be the same or different and are hydrogen or lower alkyl containing 1 to 8 carbons, with the proviso that at least one of $R_1$ and $R_2$ is lower alkyl, or

may be taken together to form a pyrrolidino, piperidino or morpholino ring, and $R_3$ and $R_4$ are the same or different and are hydrogen, lower alkyl containing 1 to 8 carbons, lower alkoxy containing 1 to 8 carbons, bromine, chlorine, fluorine or trifluoromethyl, and physiologically acceptable acid-addition salts thereof.

2. The compound of claim 1 wherein $R_1$ and $R_2$ are each lower alkyl.

3. The compound of claim 1 wherein $R_1$ is hydrogen and $R_2$ is lower alkyl.

4. The compound of claim 1 wherein

represents pyrrolidino, piperidino or morpholino.

5. The compound of claim 1 wherein $(CH_2)_n$ is —$(CH_2)_2$— or —$(CH_2)_3$—.

6. The compound of claim 1 having the name 1-[2-(dimethylamino)ethyl]-1,2-dihydro-2-oxo-4-phenyl-3-quinolinecarbonitrile or its hydrochloride salt.

7. The compound of claim 1 having the name 1-[3-(dimethylamino)propyl]-1,2-dihydro-2-oxo-4-phenyl-3-quinolinecarbonitrile or its hydrochloride salt.

8. An anti-inflammatory composition comprising an anti-inflammatory amount of a compound as defined in claim 1 and a pharmaceutically acceptable carrier therefor.

9. A method for treating an inflammatory condition, which comprises administering to a mammalian host an anti-inflammatory amount of a compound as defined in claim 1.

* * * * *